United States Patent [19]

Hausladen et al.

[11] Patent Number: 5,866,709
[45] Date of Patent: *Feb. 2, 1999

[54] PROCESS FOR MAKING AROMATIC NITRILES

[75] Inventors: Michael C. Hausladen, Eggertsville; Bao-Guo Huang, Cheektowaga; David Y. Tang, East Amherst, all of N.Y.

[73] Assignee: Occidental Chemical Corp, Niagara Falls, N.Y.

[ * ] Notice: The term of this patent shall not extend beyond the expiration date of Pat. No. 5,760,274.

[21] Appl. No.: 982,611

[22] Filed: Dec. 2, 1997

[51] Int. Cl.⁶ .................... C07C 253/00; C07C 255/00
[52] U.S. Cl. ............................................ 558/329; 558/425
[58] Field of Search ...................................... 558/329, 425

[56] References Cited

U.S. PATENT DOCUMENTS 5,760,274  6/1998  Spohn et al. ............................. 558/329

FOREIGN PATENT DOCUMENTS

0441004 B1  9/1995  European Pat. Off. .
2550261A    5/1977  Germany .
8119925 AZ  5/1996  Japan .
53059645   10/1996  Japan .

*Primary Examiner*—Johann Richter
*Assistant Examiner*—Joseph Murray
*Attorney, Agent, or Firm*—Richard D. Fuerle

[57] ABSTRACT

Disclosed is a process for making an aromatic nitrile by reacting a benzotrichloride with an ammonium halide in the presence of an oxygen-donating initiator at a temperature of about 150° to about 250° C. An optional catalyst of a metal oxide or a metal salt can be used if desired.

21 Claims, No Drawings

PROCESS FOR MAKING AROMATIC NITRILES

BACKGROUND OF THE INVENTION

This invention relates to a process for making an aromatic nitriles from a benzotrihalide and an ammonium halide. In particular, it relates to such a process in which a small amount of an oxygen-donating initiator is used.

Aromatic nitriles are important intermediates in the dye and pharmaceutical industries. At the present time, benzonitrile and chlorinated benzonitriles are made on an industrial scale by reacting benzotrichloride or a chlorinated benzotrichloride, respectively, with ammonia gas, ammonium hydroxide, or ammonium chloride in the presence of a catalyst such as ferric chloride, zinc chloride, copper chloride, or copper oxide. While these reactions produce the desired product, they also produce unwanted byproducts, such as tar residues, resulting in a significant amount of solid waste. Also, some of the reactions have been found to selectively form triazine in the presence of catalysts such as ferric chloride.

SUMMARY OF THE INVENTION

We have discovered that benzotrihalides (including substituted benzotrihalides) can be reacted with an ammonium halide to form benzonitriles by using an oxygen-donating initiator. In the reaction of this invention, a catalyst is not required. Unlike prior processes for producing aromatic nitriles, the process of this invention does not produce significant amounts of solid waste and does not need a large excess of an ammonia source.

DESCRIPTION OF THE PREFERRED EMBODIMENTS

In the process of this invention, a benzotrihalide is reacted with an ammonium halide in the presence of an oxygen-donating initiator. The benzotrihalide starting material has the general formula

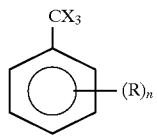

where X is Cl or Br, R is halide, aliphatic from $C_1$ to $C_8$, or aromatic from $C_6$ to $C_8$, and n is 0 to 5. The X group is preferably chlorine because benzotrichlorides are less expensive than other benzotrihalides. The R group is preferably chlorine or alkyl from $C_1$ to $C_5$ as those benzotrihalides are more readily available, and n is preferably 1 to 3 as those benzotrihalides are more important commercially at the present time. (It should be noted that the general formula is intended to cover only compounds that can be made, as some of the multiply substituted benzotrihalides cannot be made at this time.) Examples of compounds within the general formula include benzotrichloride (BTC), o-chlorobenzotrichloride (OCBTC), p-chlorobenzotrichloride (PCBTC), m-chlorobenzotrichloride, 2,4-dichlorobenzotrichloride (2,4-DCBTC), 3,4-dichlorobenzotrichloride (3,4-DCBTC), 3,5-dichlorobenzotrichloride, benzotribromide, o-chlorobenzotribromide, m-trifluorotrichloroxylene, and m-hexachloroxylene. The preferred compounds are BTC, OCBTC, PCBTC, and 3,4-DCBTC, because those compounds make commercially important nitriles.

The benzotrihalide is reacted with an ammonium halide, which can be ammonium chloride, ammonium bromide, or ammonium fluoride. Ammonium chloride and ammonium bromide are preferred and ammonium chloride is particularly preferred as it is inexpensive. The ammonium halide can be formed in situ by the reaction of gaseous ammonia with the hydrogen halide byproduct of the reaction. The amount of ammonium halide can be within about 50 mole % of stoichiometric with the amount of benzotrihalide as the reaction proceeds well in that range; it is preferably within about 20 mole % of stoichiometric and is most preferably stoichiometric or up to about 5 mole % in excess of stoichiometric.

The reaction must be performed in the presence of an initiator as it will not proceed at a significant rate in the absence of an initiator. The initiator is an acid halide or a compound that can react with benzotrihalide or a substituted benzotrihalide to form the corresponding acid halide. Examples of initiators include benzoic acid, benzamide, benzoic acid anhydride, and benzoyl chloride. The initiator can be formed in situ by adding a compound, such as water, ammonium hydroxide, or magnesium oxide, that will react with the benzotrihalide to form an acid chloride.

The preferred initiators (or compounds that form initiators in situ) react with the ammonium halide to form the desired nitrile product, thereby increasing product yield and avoiding the production of a mixture of nitriles. If the initiator is an acid, acid chloride, or amide it preferably corresponds to the product nitrile so that it will be converted into the desired product. For example, if the desired product is o-chlorobenzonitrile (OCBN), the preferred initiators are water, o-chlorobenzoic acid (OCBA), o-chlorobenzoyl chloride (OCBOC), or o-chlorobenamide (OCBAM) because those initiators will react with OCBTC and the ammonium halide to form OCBN.

The amount of initiator is critical to the success of the reaction. If too much initiator is present, the reaction rate is faster but a significant amount of the corresponding acid and amide will be formed as well as the desired nitrile. If too little initiator is present, the reaction may take so long as to be impractical. We have found that the amount of initiator available to the reaction must be between 0.001 and 0.25 equivalents in order to avoid the ill effects of too little or too much initiator. For best results, the amount initiator should be between 0.02 and 0.15 equivalents. Since some initiators (or compounds that form initiators), such as water, may evaporate if the reaction is not performed under pressure, the amount of initiator should be calculated as the amount that is available to the reactants and not the amount that is placed in the reaction mixture or formed in situ in the reaction mixture.

Preferably, no catalyst is used in the process of this invention because we have found that a catalyst increases the amount of tar produced and can change the selectivity so that in some cases more triazine is made. However, if desired, an optional catalyst can be used to increase the reaction rate. Catalysts that can be used in the reaction of this invention are metal salts (e.g., halides) and metal oxides of Groups IB, IIB, IIIA, IIA, and VIII of the Periodic Table. Zinc chloride and copper chloride are the preferred catalysts because they work well at ppm levels. When making p-chlorobenzonitrile (PCBN) and 3,4-dichlorobenzonitrile (3,4-DCBN) ferric chloride is not preferred because it increases the formation of triazine. Up to about 5 wt % catalyst can be used, based on the weight of the benzotrihalide, and the preferred amount of catalyst is about 100 ppm to about 1 wt % as less has little effect and more may cause the reaction to be too fast to control.

The reaction is performed by simply mixing together the benzotrihalide or substituted benzotrihalide, the ammonium halide, the initiator, and the catalyst if one is used. The reactants are heated to a temperature of about 150° to about 250° C. as at lower temperatures the reaction rate is too slow and at higher temperatures byproducts and tar may form; the preferred temperature range is about 180° to about 230° C. The desired nitrile product has the general formula:

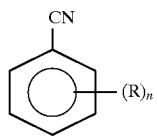

The nitrile product can be recovered from the reaction mixture by distillation.

The following examples further illustrates this invention.

EXAMPLE 1

OCBTC (230 g, 1.0 mol), ammonium chloride (59 g, 1.10 eq), and OCBA (15.7 g) were added to a 500 mL reactor equipped with thermocouple, overhead stirrer, and reflux condenser. The reaction mixture was stirred, heated up to 225° C., and maintained at that temperature while the reaction was periodically followed by gas chromatography (GC). After a reaction time of about 8 h, OCBN (121.5 g, 88.4%) was obtained by distillation (melting point: 45°–46° C.).

EXAMPLE 2

The reaction was carried out as described in Example 1. PCBTC (230 g, 1.0 mol), ammonium chloride (56.2 g, 1.05 eq), and p-chlorobenzoic acid (11.5 g) were charged to the reactor. The mixture was heated at 215° C. for 9 h. Distillation of the reaction mixture gave PCBN (122.4 g, 89%, melting point: 92°–93° C.).

EXAMPLE 3

The reaction was performed as in Example 1. The following reactants were charged to the reactor: 2,4-DCBTC (132.8 g, 0.5 mol), ammonium chloride (28.1 g, 1.05 eq), and 2,4-dichlorobenzoyl chloride (13.3 g). The mixture was heated at 230° C. for 14 h. Distillation of the reaction mixture gave pure 2,4-dichlorobenzonitrile (2,4-DCBN) (76.4 g, 89% yield, melting point: 59°–60° C.).

EXAMPLE 4

The reaction was carried out as described in Example 1. BTC (195.5 g, 1.0 mol), ammonium chloride (56.1 g, 1.05 eq), and benzoyl chloride (20 g) were charged to the reactor. The mixture was heated at 190° C. for 15 h. The GC yield of BN was 92.3%.

EXAMPLE 5

Example 1 was repeated using OCBTC (230 g, 1.0 mol), ammonium chloride (59 g, 1.10 eq), and water (4.6 g, 2%). The mixture was heated up to 215° C. Most of water was distilled off from the reactor. The reaction mixture was then maintained at 215° C. for 22 h. Distillation of the reaction mixture gave pure OCBN (125.2 g, 91%).

EXAMPLE 6

The reaction was performed as in Example 1 except that the following reactants were charged to the reactor: OCBTC (230 g, 1.0 mol), ammonium chloride (59 g, 1.10 eq), and o-chlorobenzoyl chloride (35 g). The mixture was heated at 225° C. for 10 h. The GC yield of OCBN was 89.6%.

EXAMPLE 7

The reaction was carried out as in Example 1. The following reactants were charged to the reactor: OCBTC (90 g, 0.39 mol), ammonium chloride (23 g, 1.10 eq), and o-chlorobenzamide (9 g). The mixture was heated at 225° C. for 11 h. The GC yield of OCBN was 92.4%.

EXAMPLE 8

The reaction was performed as in Example 1. OCBTC (230 g, 1.0 mol), ammonium chloride (59 g, 1.10 eq), OCBA (15.6 g), and zinc acetate (460 mg, 0.2%) were charged to the reactor. The mixture was heated at 225° C. for 5 h. The GC yield of OCBN was 90.5%.

EXAMPLE 9

The reaction was carried out as in Example 1. The following reactants were charged to the reactor: OCBTC (233.5 g, 1.02 mol), ammonium chloride (54.8 g, 1.0 eq), OCBA (13.87 g), and anhydrous ferric chloride (70.9 mg, 300 ppm). The mixture was heated at 215° C. for 5 h. The GC yield of OCBN was 85.1%.

EXAMPLE 10

OCBTC (406 G, 1.76 mol) and OCBA (32.75 g, 0.21 mol) were added to a 500 mL flask equipped with a thermocouple, overhead stirrer, reflux condenser, and $NH_3$ blow tube. The reaction mixture was heated to 225° C. and the flow of $NH_3$ (70–100 mL/min) was started through the blow tube, forming $NH_4Cl$ in situ. After 8 hours, GC indicated that all the OCBTC had reacted. The reaction mixture was distilled, obtaining 224 g of OCBN (95% by GC, mp 45° C.).

We claim:

1. A method of making an aromatic nitrile having the general formula

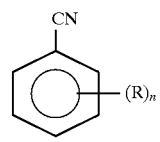

comprising
(A) preparing a mixture which comprises
(1) a benzotrihalide having the general formula

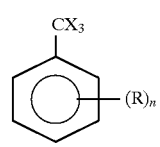

where X is chlorine or bromine, R is halide or aliphatic or aromatic from $C_1$ to $C_8$, and n is 0 to 5;
(2) an ammonium halide in an amount within about 50 mole % of stoichiometric with said benzotrihalide;
(3) 0.001 to 0.25 equivalents of an oxygen-donating initiator; and
(4) up to about 5 wt % of a metal oxide or metal salt catalyst; and
(B) heating said mixture at about 150° to about 250° C.

2. A method according to claim 1 wherein said benzotrihalide is benzotrichloride.

3. A method according to claim 1 wherein said benzotrihalide is orthochlorobenzotrichloride.

4. A method according to claim 1 wherein said benzotrihalide is parachlorobenzotrichloride.

5. A method according to claim 1 wherein said benzotrihalide is 3,4-dichlorobenzotrichloride.

6. A method according to claim 1 wherein said ammonium halide is ammonium chloride.

7. A method according to claim 1 wherein said initiator reacts with said benzotrihalide and said ammonium halide to form said aromatic nitrile.

8. A method according to claim 1 wherein said initiator is the acid, acid chloride, or amide that corresponds to said aromatic nitrile.

9. A method according to claim 1 wherein said initiator is an acid chloride that is formed in situ by the reaction of water with said benzotrihalide.

10. A method according to claim 1 wherein said ammonium halide is formed in situ by the addition of gaseous ammonia to said mixture.

11. A method according to claim 1 wherein the amount of said catalyst is about 100 ppm to about 1 wt %.

12. A method according to claim 11 wherein said catalyst is zinc chloride or copper chloride.

13. A method according to claim 1 including the additional last step of recovering said aromatic nitrile from said mixture by distillation.

14. A method of making an aromatic nitrile having the general formula

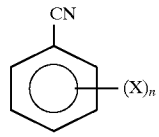

comprising
(A) preparing a mixture which comprises
   (1) a benzotrihalide having the general formulas

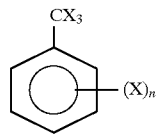

where X is halogen and n is 1 to 3;
   (2) an ammonium halide in an amount within about 20 mole % of stoichiometric with said benzotrihalide;
   (3) 0.001 to 0.25 equivalents of an oxygen-donating initiator that reacts with said benzotrihalide and said ammonium halide to form said aromatic nitrile; and
   (4) up to about 5 wt % of a metal oxide or metal salt catalyst; and (B) heating said mixture at about 150° to about 250° C.

15. A method according to claim 14 wherein said initiator is the acid, acid chloride, or amide that corresponds to said aromatic nitrile.

16. A method of making an aromatic nitrile having the general formula

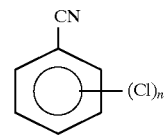

comprising
(A) preparing a mixture which comprises
   (1) a chlorobenzotrichloride having the general formula

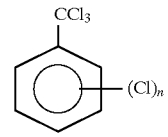

where n is 1 to 3;
   (2) ammonium chloride in an amount between stoichiometric and up to about 5 mole % in excess of stoichiometric with said chlorobenzotrichloride;
   (3) about 0.02 to about 0.15 equivalents of an initiator selected from the group consisting of the acid, acid chloride, and amide that corresponds to said aromatic nitrile, which reacts with said chlorobenzotrichloride and said ammonium chloride to form said aromatic nitrile; and
   (4) up to about 5 wt % of a metal oxide or metal salt catalyst;

(B) heating said mixture at about 180° to about 230° C.; and (C) recovering said aromatic nitrile from said mixture by distillation.

17. A method according to claim 16 wherein said chlorobenzotrichloride is orthochlorobenzotrichloride.

18. A method according to claim 16 wherein said chlorobenzotrichloride is parachlorobenzotrichloride.

19. A method according to claim 16 wherein said chlorobenzotrichloride is 3,4-dichlorobenzotrichloride.

20. A method according to claim 16 wherein said catalyst is about 100 ppm to about 1 wt %, based on the weight of said chlorobenzotrichloride, zinc chloride or copper chloride.

21. A method according to claim 1 wherein said mixture contains no metal oxide or metal salt catalyst.

* * * * *